US009528105B2

(12) United States Patent
Chen et al.

(10) Patent No.: US 9,528,105 B2
(45) Date of Patent: Dec. 27, 2016

(54) NUCLEIC ACID EXTRACTION USING ORGANIC SOLVENTS TO REMOVE INHIBITORS

(71) Applicant: TECHLAB INC., Blacksburg, VA (US)

(72) Inventors: Li Chen, Blacksburg, VA (US); Jodie Stevens, Christianburg, VA (US); Kristen Schwab, Christiansburg, VA (US); James Boone, Christiansburg, VA (US); David Lyerly, Radford, VA (US)

(73) Assignee: TECHLAB, INC., Blacksburg, VA (US)

( * ) Notice: Subject to any disclaimer, the term of this patent is extended or adjusted under 35 U.S.C. 154(b) by 0 days.

(21) Appl. No.: 14/845,124

(22) Filed: Sep. 3, 2015

(65) Prior Publication Data

US 2016/0138009 A1 May 19, 2016

Related U.S. Application Data

(60) Provisional application No. 62/045,888, filed on Sep. 4, 2014.

(51) Int. Cl.
*C07H 21/02* (2006.01)
*C12Q 1/68* (2006.01)
*C12N 15/10* (2006.01)

(52) U.S. Cl.
CPC ......... *C12N 15/1003* (2013.01); *C12Q 1/6806* (2013.01)

(58) Field of Classification Search
None
See application file for complete search history.

(56) References Cited

U.S. PATENT DOCUMENTS

| 7,459,548 B2 | 12/2008 | Brolaski et al. |
| 2006/0177837 A1 | 8/2006 | Borozan et al. |
| 2008/0003564 A1 | 1/2008 | Chen et al. |
| 2011/0318240 A1* | 12/2011 | Boone .............. G01N 33/54366 422/402 |
| 2013/0273642 A1 | 10/2013 | Boone et al. |
| 2015/0104803 A1 | 4/2015 | Birnboim |

OTHER PUBLICATIONS

International Search Report with Written Opinion dated Nov. 30, 2015 in Application No. PCT/US15/48628, 11 pages.

* cited by examiner

*Primary Examiner* — Michael Burkhart
(74) *Attorney, Agent, or Firm* — Shook, Hardy & Bacon L.L.P.

(57) ABSTRACT

Nucleic acid amplification tests have been widely used in clinical laboratories. Nucleic acid extraction from biological materials is challenging because different unfavorable substances may co-extract and inhibit downstream applications. The present invention relates to a composition of and a method for treating the sample prior, during or post extraction of nucleic acid. More specifically, the claimed invention relates to a composition of and a method for using low concentrations of common organic solvents to remove inhibitors of nucleic acid amplification. The present invention can be used for extracting nucleic acids (DNA/RNA) from bacteria, viruses, parasites, and other biological materials or matrices, including but not limit to, stool samples, body fluids, plants and cultures. The method is rapid, low-cost, and easy to use in a laboratory setting. The nucleic acid extracted in accordance with the invention can be used for nucleic acid amplification reactions.

20 Claims, 14 Drawing Sheets

NUCLEIC ACID EXTRACTION USING ORGANIC SOLVENTS TO REMOVE INHIBITORS

CROSS-REFERENCE TO RELATED APPLICATIONS

This application claims priority to U.S. Provisional Application No. 62/045,888, filed Sep. 4, 2014, entitled "Nucleic Acid Extraction Using Organic Solvents to Remove Inhibitors," the entire contents of which are herein incorporated by reference.

BACKGROUND

The nucleic acid amplification test (NAAT) has been widely used in current molecular diagnostics, including infectious diseases, oncology, and pharmacogenomics. It provides a user-friendly and accurate result and is less time consuming compared to traditional diagnostic methods. In order to perform molecular diagnostic studies such as polymerase chain reaction (PCR) and isothermal amplification, nucleic acids are extracted from biological materials, such as stool samples and blood samples. A wide array of methods has been developed for nucleic acid extraction, producing numerous tradeoffs among costs, ease of use, time required, materials including hazardous chemicals used, and quantity and quality of extracted nucleic acids.

Current available methods require lengthy enzymatic digestions, incubations, separation and nucleic acid precipitation or elution. Also a boiling step is the most common method used for crude nucleic acid preparations. In many cases, the quality and quantity of the isolated nucleic acids are not amenable to downstream applications such as nucleic acid amplification. Preparation of nucleic acid samples prior to amplification and detection of specific targets is the most challenging step of molecular diagnostics, because a wide variety of compounds present in biological samples can degrade and denature DNA polymerase, or reduce enzymatic activity of the DNA polymerase in a PCR or an isothermal amplification reaction. Therefore, an optimal nucleic acid purification method can reduce or eliminate the inhibition of amplification by components of biological samples to achieve successful amplification. Simple and rapid methods that do not require extensive sample processing and that can be adapted to a clinical laboratory are needed for producing quality nucleic acids free of inhibitors of amplification.

BRIEF SUMMARY

The present claimed invention relates to a composition of and a method for treating the sample prior, during or post extraction of nucleic acid. More specifically, the present claimed invention relates to a composition of and a method for using low concentrations of common organic solvents to remove inhibitors of nucleic acid amplification. The claimed invention can be used for extracting nucleic acids (DNA/RNA) from bacteria, viruses, parasites, and other biological materials or matrices, including but not limit to, stool samples, body fluids, plants and cultures. The method described herein is rapid, low-cost, and easy to use in a laboratory setting. The nucleic acid extracted in accordance with the claimed invention can be used for nucleic acid amplification reactions. The object of the claimed invention is to provide an optimal nucleic acid purification method to reduce or eliminate the inhibition of amplification by components of biological samples to achieve successful amplification.

BRIEF DESCRIPTION OF SEVERAL VIEWS OF THE DRAWINGS

Illustrative embodiments of the claimed invention are described in detail below with reference to the attached drawing figures, wherein:

DETAILED DESCRIPTION

Figure 1:
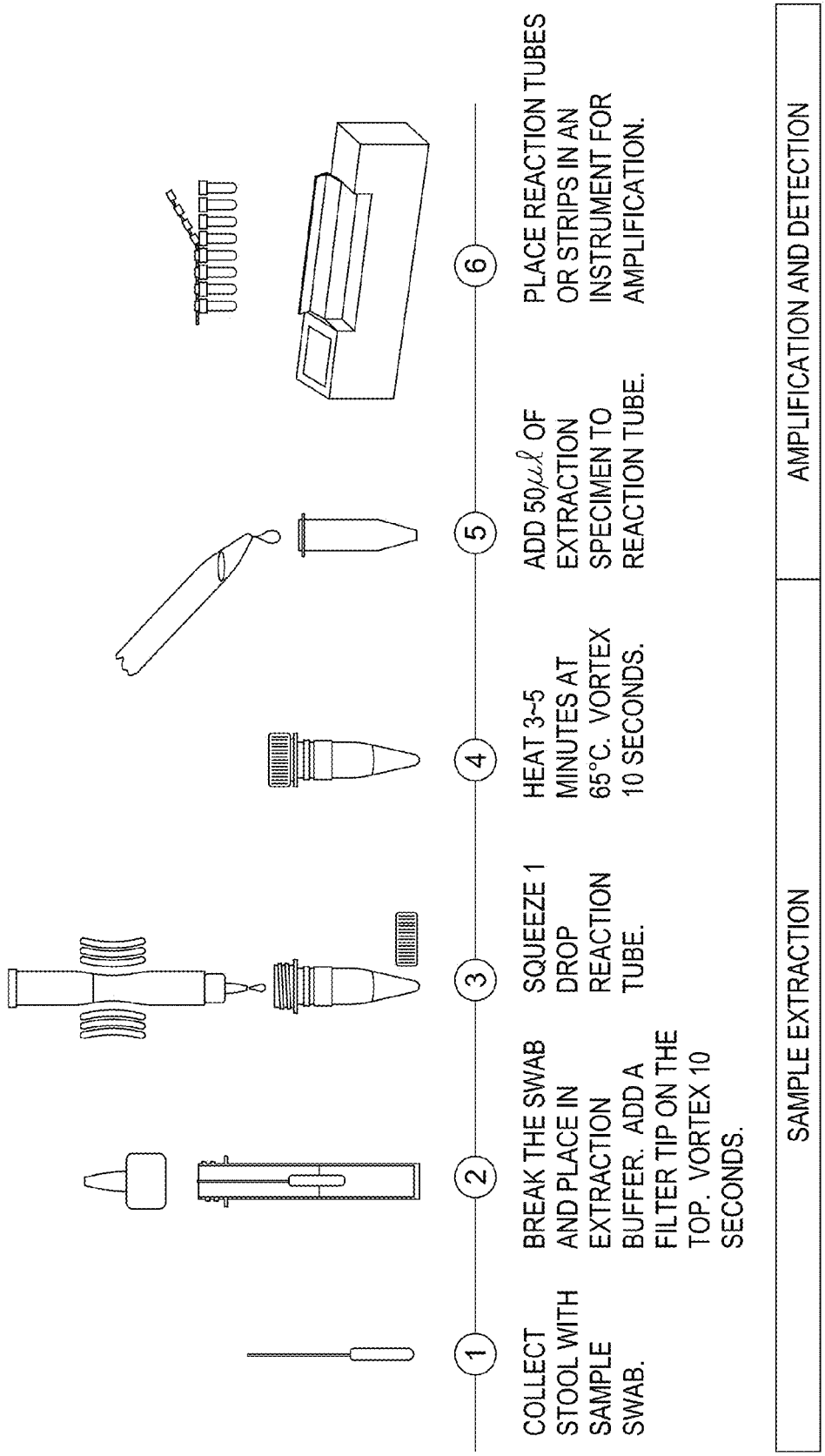
FIG. 1 illustrates exemplary steps of a novel nucleic acid extraction method that includes an organic solvent to simplify nucleic acid extraction without the need to boil biological materials.

The subject matter of the claimed invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

With the goals of speed and low cost, there is a continuing need for new materials and procedures to extract nucleic acids in less time and reduce the risk of operator intervention and error. Human specimens such as stool and blood represent a great challenge for sample preparation prior to downstream molecular applications due to the presence of various inhibitors. In addition, eliminating these inhibitors of nucleic acid amplification by boiling is not suitable for molecular tests requiring purified RNA because heating leads to degradation of RNA. Inhibitors that are found in human specimens and that affect both PCR and isothermal amplification include bile salts, complex polysaccharides, hemoglobin/hemin, polyphenols, pigments, and urea. Much effort has been devoted to the development of sample preparation methods to overcome the problem of these DNA amplification inhibitors, and various techniques have been employed to reduce the effect of inhibitors. For example, aqueous two-phase systems, filtration, dilution, and filtration have been used to facilitate DNA amplification. Ten minute boiling is also a very common method used for crude bacteria DNA preparation, which is very effective to lyse cells to release nucleic acid and to reduce inhibition on downstream amplifications. However, boiling samples in a clinical laboratory is not safe or convenient. Thus there is a need for a safer and easier method for crude nucleic acid extraction as the existing methods are labor-intensive, complex, and/or costly. As a result, they are not practical in many clinical laboratory settings. Thus, there is an urgent need for a simple, easy-to-use method that extracts high quality nucleic acids from biological specimens.

A novel sample preparation method is described herein that uses low concentrations of organic solvents combined with a short and lower temperature incubation to replace boiling and other extensive steps (such as enzymatic digestion, incubation, separation, precipitation, and elution) that are widely used in nucleic acid extraction procedures to effectively eliminate the inhibitory factors in the nucleic acids extracted from biological materials. The method of the claimed invention can be used with different biological samples such as blood, stool, urine, plants, etc. The addition of a low concentration of organic solvents in the nucleic acid extraction buffer lowers the temperature required for DNA preparations and RNA extractions because boiling is no longer needed to eliminate inhibition of amplification in crude nucleic acid preparations. The addition of organic solvents can be used to treat the sample prior to, during, and after nucleic acid extraction methods. A single solvent or combination of solvents can be used. The extraction buffer robustly lyses cells, resulting in the release of nucleic acid into the extraction buffer. Organic solvents help to reduce or remove inhibition of amplification at a lower temperature in crude nucleic acid preparation. Combined with filtration through either activated charcoal or regular filters, inhibitors in the samples are bound to the filter and/or dissolved/denatured in the buffer. The nucleic acid extracted in accordance with the present method is suitable for subsequent use in widely utilized techniques such as nucleic acid amplification. As used herein, a low concentration of organic solvent refers to a concentration below a predetermined threshold. Exemplary amounts are provided herein.

Embodiments of the claimed invention are directed to a process for preparing biological samples intended for use with isothermal amplification and PCR using a low concentration of an organic solvent to eliminate inhibitors of nucleic acid amplification.

Biological samples include biological tissues, extracts of biological tissues, and biological excretions, blood or a portion of blood, urine, feces, saliva, sputum, mucous, semen, or homogenized tissue. It thus can be a biological sample of human or animal tissue, such as homogenized meat (e.g., hamburger, lamb, pork, chicken, fish, egg). It also may be an extract of a solid specimen, such as an aqueous extract of a fecal sample or of a consumable meat sample. In addition, biological samples include plant tissues, cultured bacteria, cultured viruses, cultured parasites, and cultured mammalian and insect cells.

In accordance with one aspect of the claimed invention, a composition is provided which is capable of (i) removing or inactivating compounds present in the biological materials that may interfere with the use of the nucleic acid for downstream applications and (ii) extracting nucleic acid from biological samples.

Referring to FIG. 1, the process includes one aqueous nucleic acid extraction buffer containing a low percentage of organic solvent allowing the option of not heating, specifically not 95° C. or above. Referring to FIG. 1, a swab of sample is obtained at step 1. At step 2, the sample is added to a squeeze tube containing the nucleic acid extraction buffer with a low percentage of organic solvent, and snapped at a scored line. Still at step 2, an activated charcoal filter tip is placed on the top of the squeeze tube and the squeeze tube is vortexed for 10 seconds. At step 3, one drop of the filtered extraction specimen is squeezed out into a reaction tube. The capped reaction tube is incubated at 65 degrees Celsius for 3 minutes and vortexed for 10 seconds at step 4. The nucleic acid in the reaction tube is then ready for down-stream applications. For example, as shown in steps 5-6, 50 µl of extraction specimen or appropriate volume of extraction specimen can be used for isothermal amplification or PCR. FIG. 1 is merely exemplary in nature and may include modifications in additional embodiments of the present invention. For instance, the amount of time to heat the sample may fall within a range different than 3-5 minutes.

Figure 2:
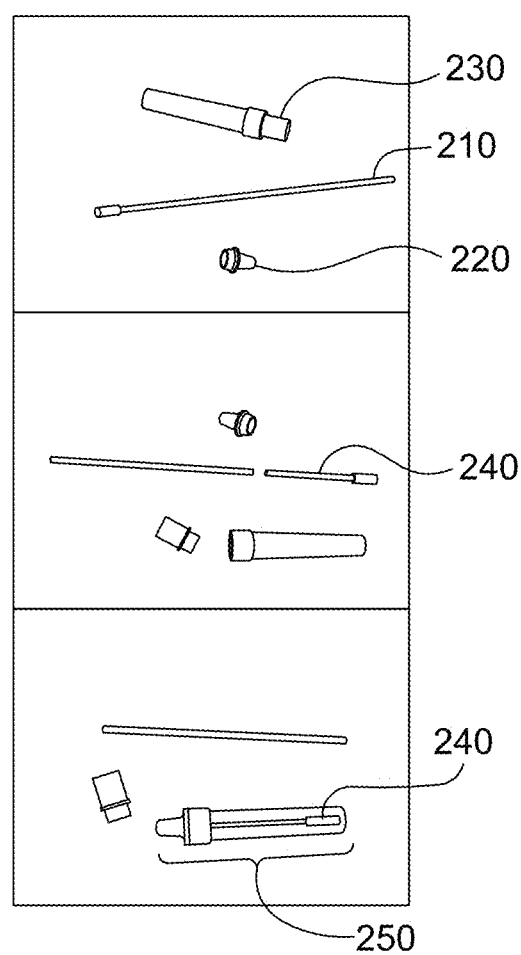
FIG. 2 illustrates an assembly of an exemplary sample collection device used in accordance with aspects of the claimed invention.

Turning now to FIG. 2, diagram 200 depicts the assembly of the sample collection device used in the claimed invention. The sample collection device comprises: a swab to collect the sample 210, a filter tip 220 that can be added to the top of an extraction tube 230. The extraction tube 230 contains extraction buffer used for nucleic acid extraction. The swab can be added to the extraction tube and snapped at the scored line 240 and left inside the extraction tube 230. After placing the snapped swab 240 inside the extraction tube 230, the filter tip 220 can be added to the top of the extraction tube 230 to assemble the sample collection device 250.

One embodiment of the claimed invention discloses a method for preparing nucleic acids from a biological sample, particularly samples of stool, blood, saliva, urine, or plant tissue. The biological sample may be diluted in the extraction buffer that contains a low percentage (about 0.5% to 20% by weight) of common organic solvents.

A low percentage of common organic solvents are suitable for inclusion in the nucleic acid extraction buffer in the practice of this claimed invention. Examples are, but are not limited to ethanol, acetone, methanol, isopropanol, and dimethyl sulfoxide (DMSO). These organic solvents, either individually or together as a mixture, are of particular interest. The concentration of the organic solvents to which biological samples are exposed can vary, but the concentration which can effectively remove inhibition will generally range from about 0.5% to about 20%, and in many cases from about 3% to about 10%, all by weight. Also the organic solvents can be used to either pre-treat the biological samples prior to nucleic acid extraction, or added to extraction buffer, or added prior to dilution before amplification. The addition of organic solvents outside a range of 0.5-20% is not advantageous because it suppresses nucleic acid amplification.

The biological sample in the extraction buffer is incubated at a temperature from about 15° C. to about 35° C. for about five seconds to about thirty minutes, to cause nucleic acids to be released into the sample fluid. An activated charcoal filter, such as Porex glass fiber filter embedded with activated charcoal is used as a filter (the pore size of the active charcoal filter may be larger than 50 µm and smaller than 250 µm). The released nucleic acids are diluted in PBS or water or appropriate amplification reaction buffers for downstream applications and the mixture is incubated for 1 to 10 minutes at 25° C. to 70° C.

Downstream applications include but are not limited to isothermal amplification, PCR (real time PCR or conventional PCR), sequencing, genotyping, and hybridization. Isothermal amplification includes, but is not limited to nicking enzyme associated reaction (NEAR), recombinase polymerase amplification (RPA), loop mediated isothermal amplification (LAMP), strand displacement amplification, helicase-dependent amplification, rolling circle amplification, and other isothermal amplification methods. Amplification is done with the extraction sample containing a low concentration of organic solvent with or without heat. The nucleic acid extraction buffer can consist of typically used buffer components.

Illustrative embodiments of the claimed invention are described in detail below with reference to the following examples, which are offered by the way of illustration and are not intended to limit the claimed invention in any manner. PCR and isothermal amplifications described below are utilized to assess the quality and quantity of extracted nucleic acids.

Example 1

Figure 3A:
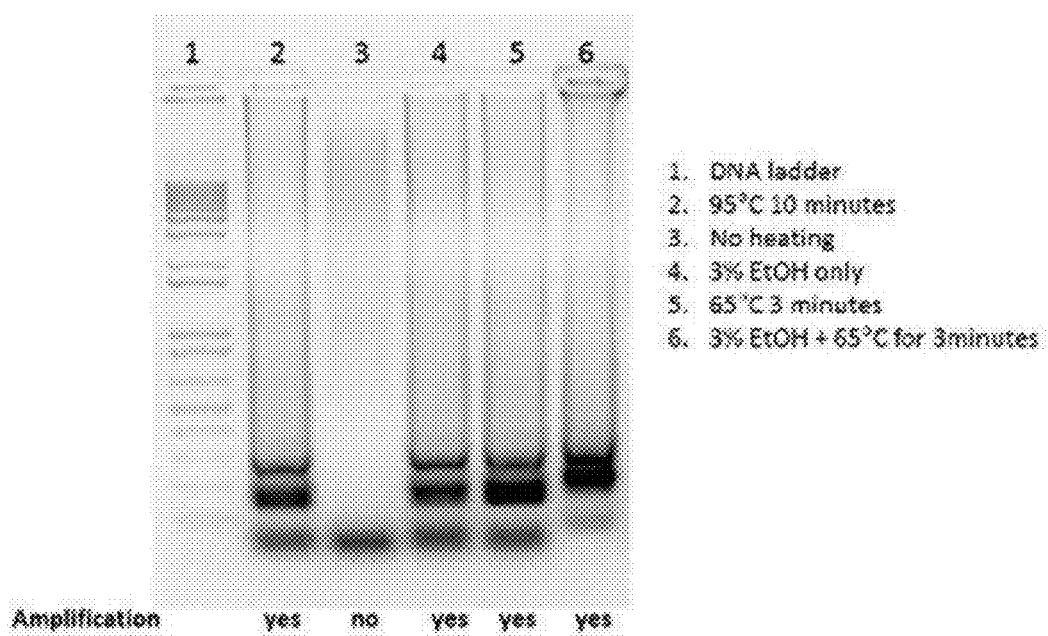
FIGS. 3A-3B depict a Coomassie Blue-stained SDS-polyacrylamide gel of isothermal amplification using crude DNA extracted from different samples using the method of the claimed invention.
Figure 3B:
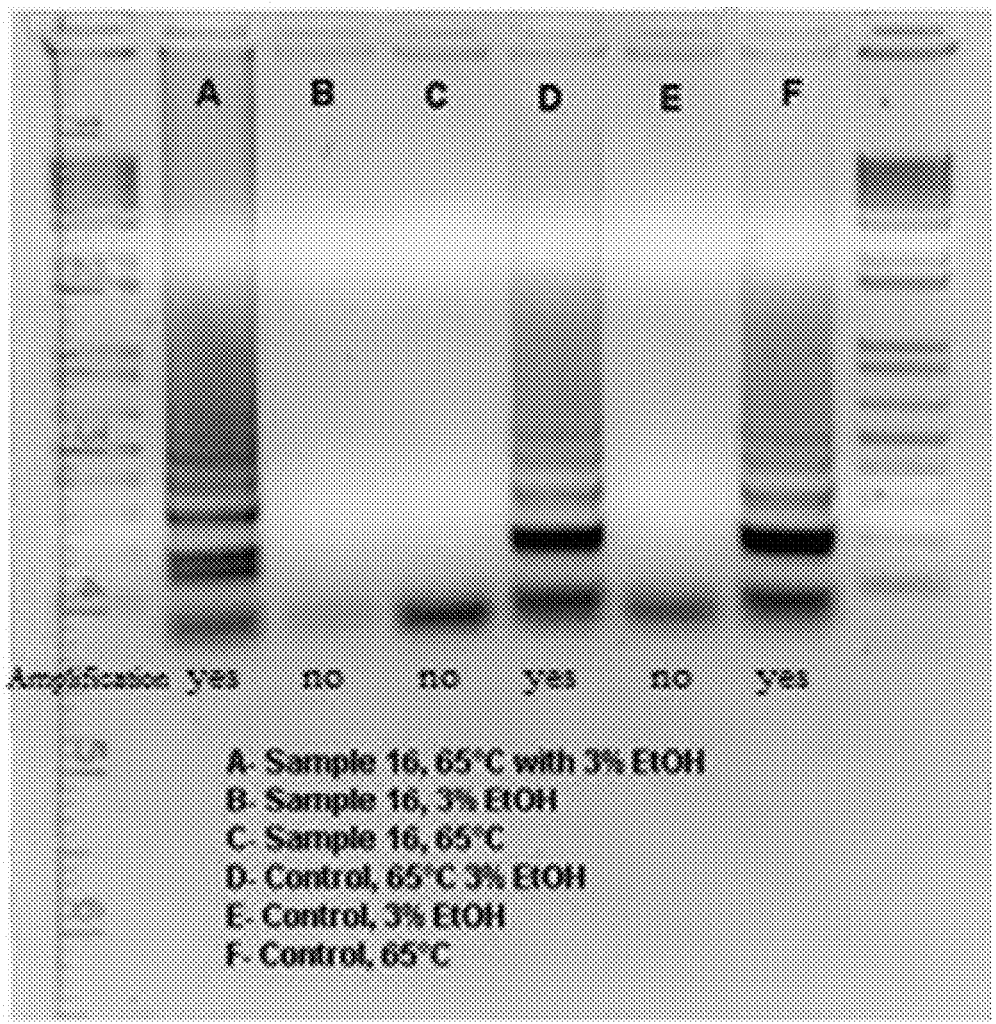

Comparison of Boiling Versus Lower Temperature Heating with Organic Solvents for Reducing or Removing Inhibitors of Nucleic Acid Isothermal Amplification A commercial *C. difficile* test was used to assess the described method of nucleic acid extraction. Different extraction conditions were tested, including boiling, no heating, or 65° C. with or without a 3% of organic solvent, to prepare nucleic acids from stool specimens for isothermal amplification. This test contains amplification of a target (tcdB gene) and internal control (IC) as illustrated in FIG. 3. FIG. 3A illustrates isothermal amplification using crude DNA extracted from a *C. difficile* positive stool sample (Sample 10233) under the listed conditions. The reactions were conducted on a heat block and amplification products were separated on a 1% agarose gel. The results are provided in FIGS. 3A (Sample 10233) and 3B (Sample 16). When the DNA was prepared with no heating (lane 3), no amplicon of tcdB gene was observed (as illustrated in FIG. 3A). In FIG. 3A, when the DNA was prepared by using boiling (lane 2), addition of 3% ethanol (lane 4), or 3 minutes of heating at 65° C. without addition of the organic solvent (lane 5), the intensity of the amplified DNA fragments was similar in the gel. FIG. 3B shows isothermal amplification using crude DNA that was extracted from Sample 16 under the indicated conditions. Amplification of tcdB gene was examined in lanes A-C of FIG. 3B. Amplification of internal control was assessed in lanes D-F of FIG. 3B. Amplification products were separated on a 1% agarose gel. As shown in FIG. 3B, when Sample 16 was treated with 3% ethanol in the extraction buffer at 65° C. for 3 minutes, the tcdB gene and internal control showed strong amplification (FIG. 3B, lanes A and D). However, when Sample 16 was treated with either 3% ethanol with no heating or 65° C. heating only, no tcdB amplification was occurred (FIG. 3B, lanes B and C). The results indicate that the 3% ethanol combined with 3-5 minutes incubation at 65° C. was optimal and comparable to the boiling in reducing the inhibition from specimens for DNA amplification. For some samples, the addition of organic solvent in extraction buffer without the heating step exhibits the same amount of amplicons as compared to the boiling method.

Example 2

Figure 4:
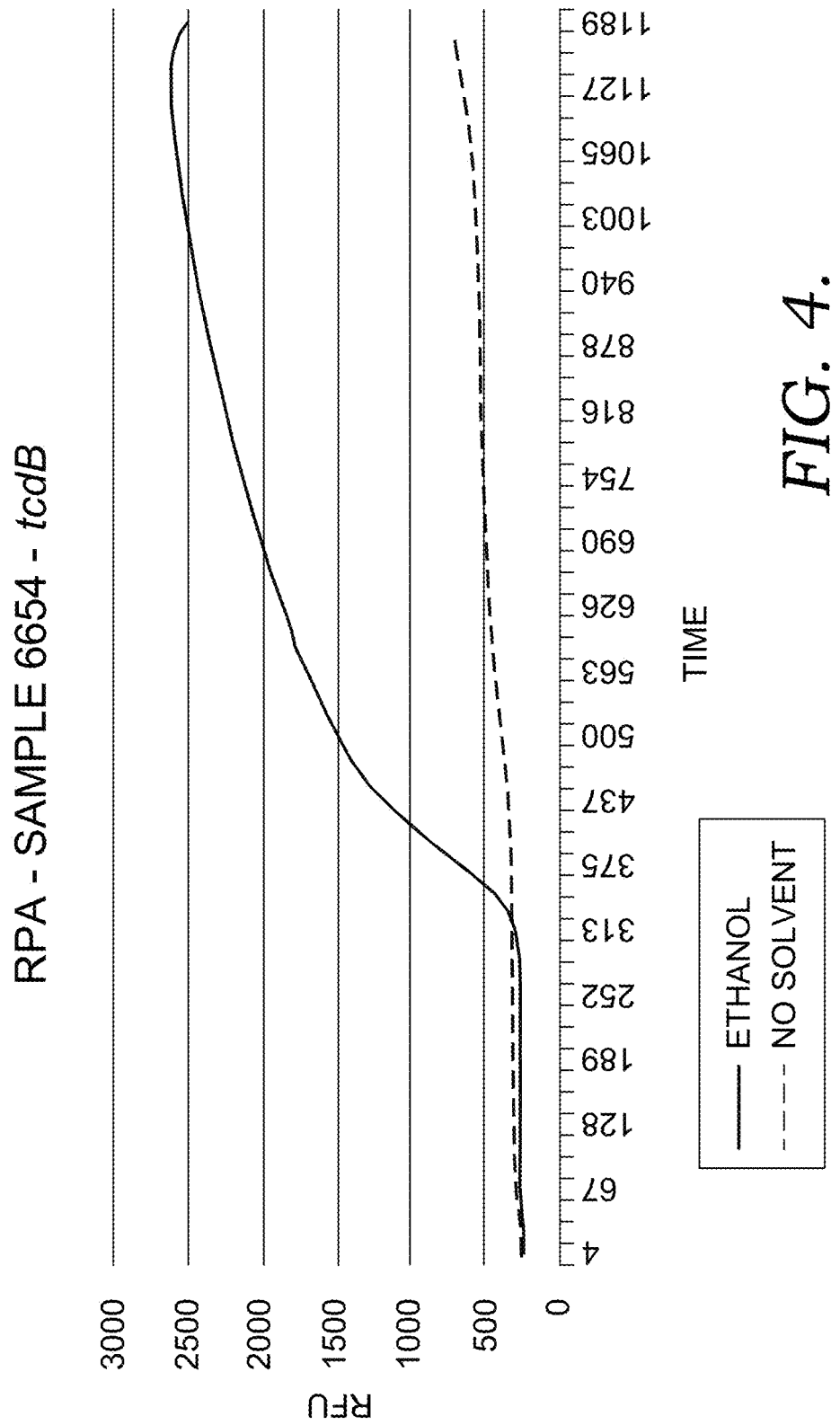
FIG. 4 depicts a graph illustrating analysis of crude DNA in a *C. difficile* RPA isothermal amplification assay.
Figure 5A:
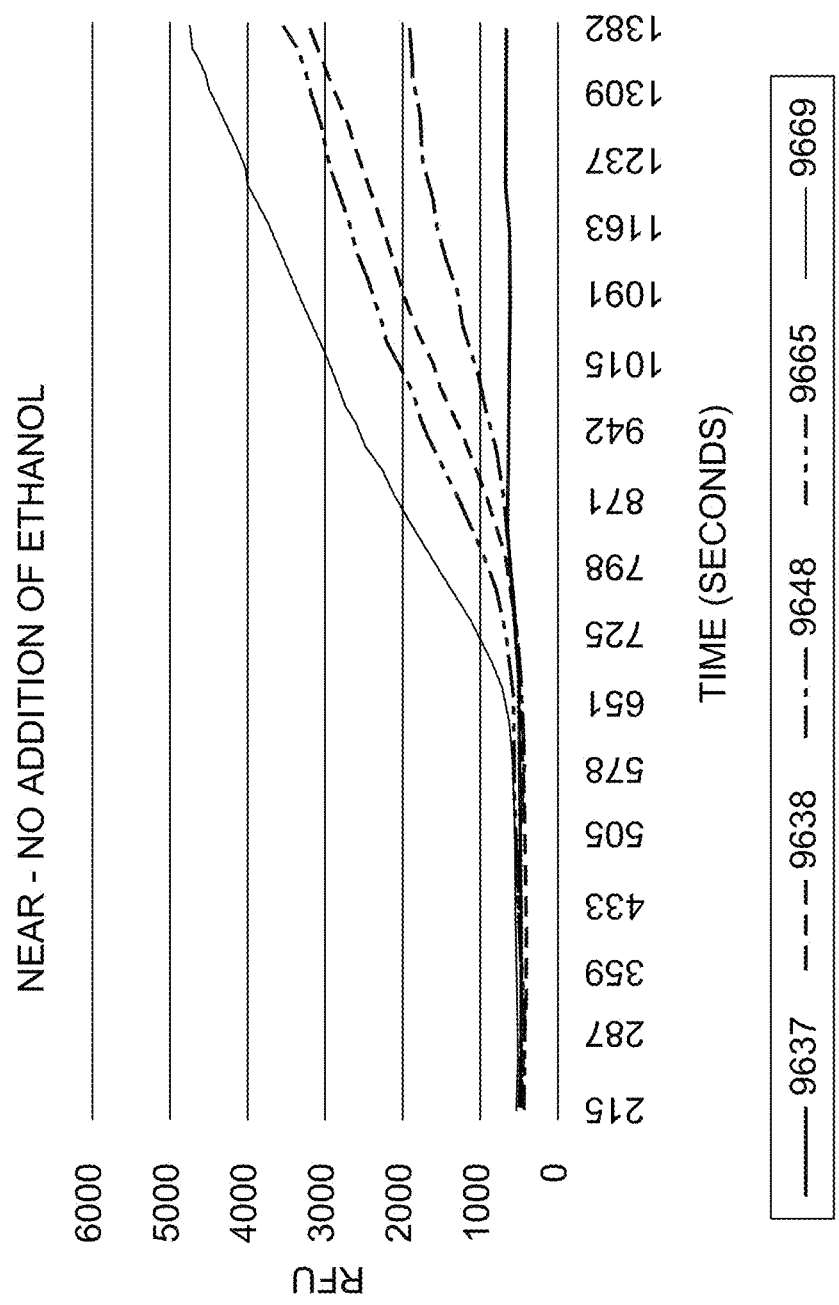
FIGS. 5A-5B depict graphs illustrating analysis of DNA extracted from stool samples using the NEAR isothermal amplification.
Figure 5B:
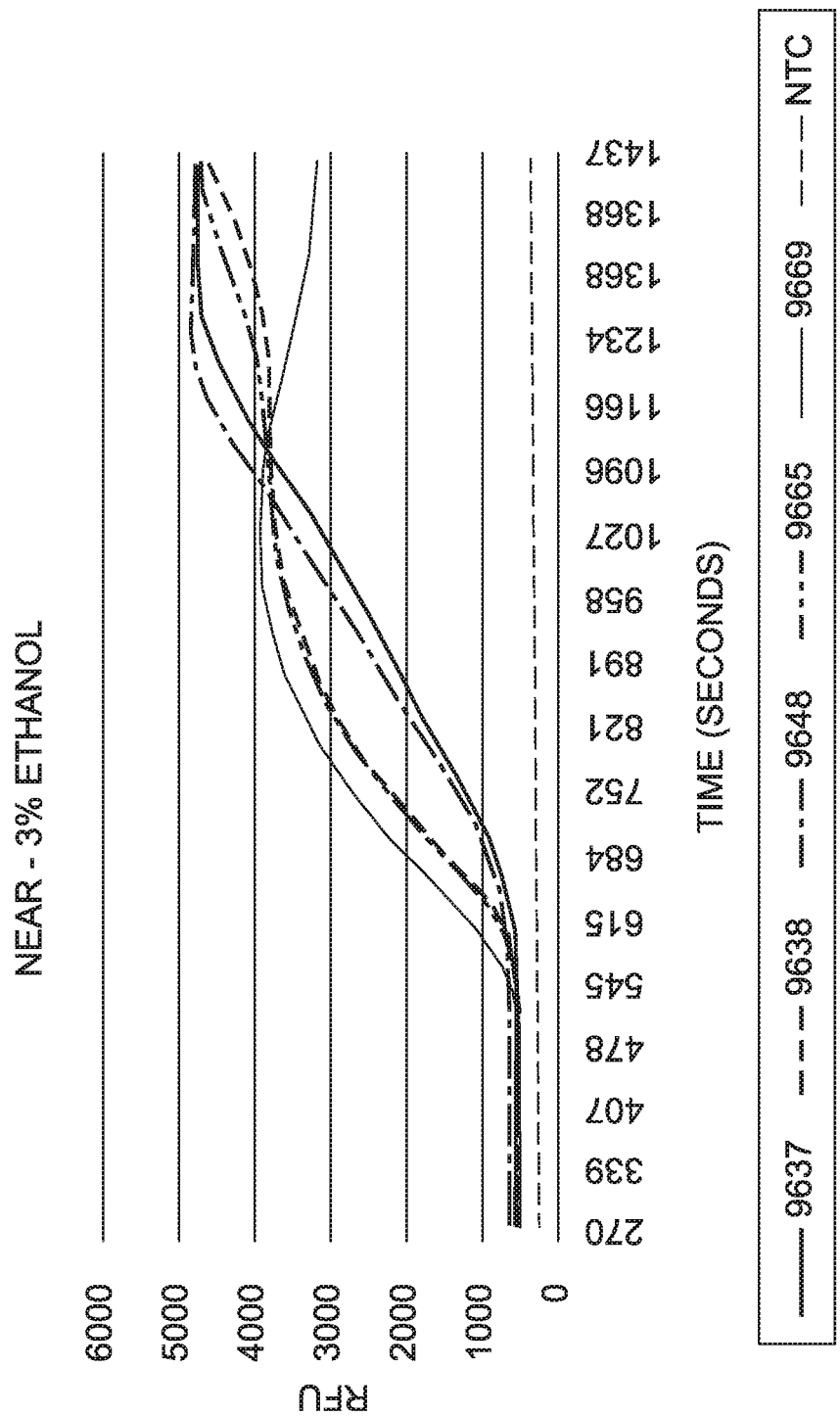

Isothermal Amplification of Nucleic Acids Extracted With or Without Ethanol Using Human Stool Samples The recombinase polymerase amplification (RPA) and the nicking enzyme associated reaction (NEAR) isothermal amplification were used to evaluate the organic solvents in reducing the inhibitory effect on nucleic acid amplification. Crude stool DNA was prepared from a patient with *C. difficile* infection (CDI) following the procedures shown in FIG. 1. The RPA *C. difficile* test was used for Sample 6654 and the NEAR *C. difficile* test was applied for Sample 9637, 9638, 9648, 9665, and 9669. The extraction buffer was used with or without addition of a 3% ethanol and was incubated at 65° C. for five minutes. The *C. difficile* toxin B gene (tcdB) was amplified from the extracted DNA sample by using the RPA and NEAR isothermal amplification. The relative amounts of the amplification products (RFU: Relative Fluorescence Unit) were measured by using an Axxin T16 fluorescence reader. The results are provided in FIG. 4 and FIG. 5. FIG. 4 illustrates analysis of crude DNA in a *C. difficile* RPA isothermal amplification assay. DNA was extracted from Sample 6654 using the extraction buffer supplemented with a 3% ethanol (solid line) or with only the extraction buffer (dash line), while FIG. 5 shows analysis of DNA extracted from stool samples using the NEAR isothermal amplification. Crude DNA was extracted from five stool samples (Samples 9637, 9638, 9648, 9665, and 9669) without (FIG. 5A) or with ethanol (FIG. 5B) in the extraction buffer. Amplification of tcdB was measured by using an Axxin T16 fluorescence reader. NTC in FIG. 5 means no template control, so no template was added to this reaction.

DNA purified from the extraction buffer containing the organic solvent (FIG. 4 solid line and FIG. 5B) gave much stronger signals and fast amplification compared to the DNA purified without the organic solvent in the extraction buffer (FIG. 4 dash line and FIG. 5A). These results indicate that inhibition of DNA amplification is substantially reduced by addition of 3% ethanol in the extraction buffer and incubation at 65° C.

Example 3

Comparison of Amplification of DNA Extracted With or Without Organic Solvent Using Human Stool Samples Containing Bacteria and Parasites The human stool samples used in this example were from patients infected with *C. difficile*, shiga-like toxin-producing *E. coli, Shigella, Campylobacter, H. pylori, Salmonella, Giardia, Cryptosporidium*, and *E. histolytica*. DNA was extracted from those clinical samples using the method described with reference to FIG. 1. DNA was also purified from those samples by using the Biomerieux NucliSENS easyMAG automated instrument and was used as controls for comparison. PCR, recombinase polymerase amplification (RPA), and nicking enzyme associated reaction (NEAR) isothermal amplification were utilized to assess the quality and quantity of extracted nucleic acids.

PCR Amplification:

PCR reactions were carried out in tubes or 96-well plates in 20 µl volumes using either IQ power mix (Bio-Rad) or SYBR greener master mix (Life Technologies). Specific primers and/or probes for each pathogen were employed in the reactions. For the SYBR master mix, PCR amplification was followed by a melting curve analysis.

A multiplex real-time PCR was conducted to detect *Giardia, Cryptosporidium*, and *E. histolytica* by using DNA purified with the method described with reference to FIG. 1. For the *Giardia, Cryptosporidium*, or *E. histolytic* positive samples, crude DNA purified with 3% of ethanol and the DNA purified by the Biomerieux NucliSENS easyMAG automated instrument showed similar DNA amplification.

Nicking Enzyme Amplification Reaction (NEAR):

NEAR reactions were carried out in 50 tl volumes using Nt.BstNBI (New England Biolabs) and Bst DNA polymerase (New England Biolabs) or Manta DNA polymerase (Enzymatics). Specific primers and probes targeting *C. difficile* toxin B gene, Shiga toxin stx1 gene and Shiga toxin stx2 gene were used in the reactions. An Axxin T16 fluorescence reader was used for detecting amplification signals. Examples for *C. difficile* positive stool samples using the NEAR test have been shown in the Example 2.

Figure 6A:
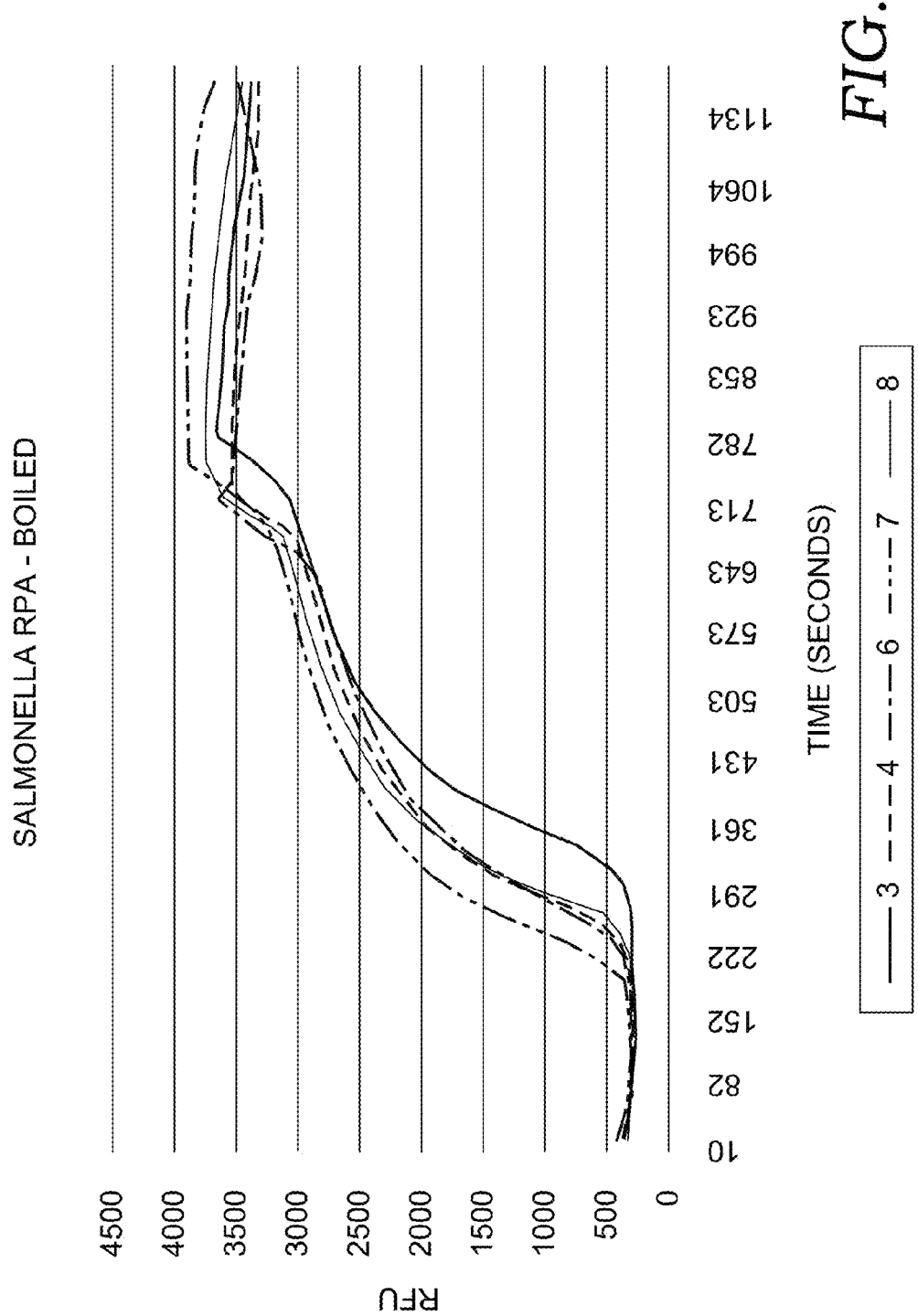
FIGS. 6A-6B depict graphs illustrating *Salmonella* RPA tests with DNA extracted from stool samples.
Figure 6B:
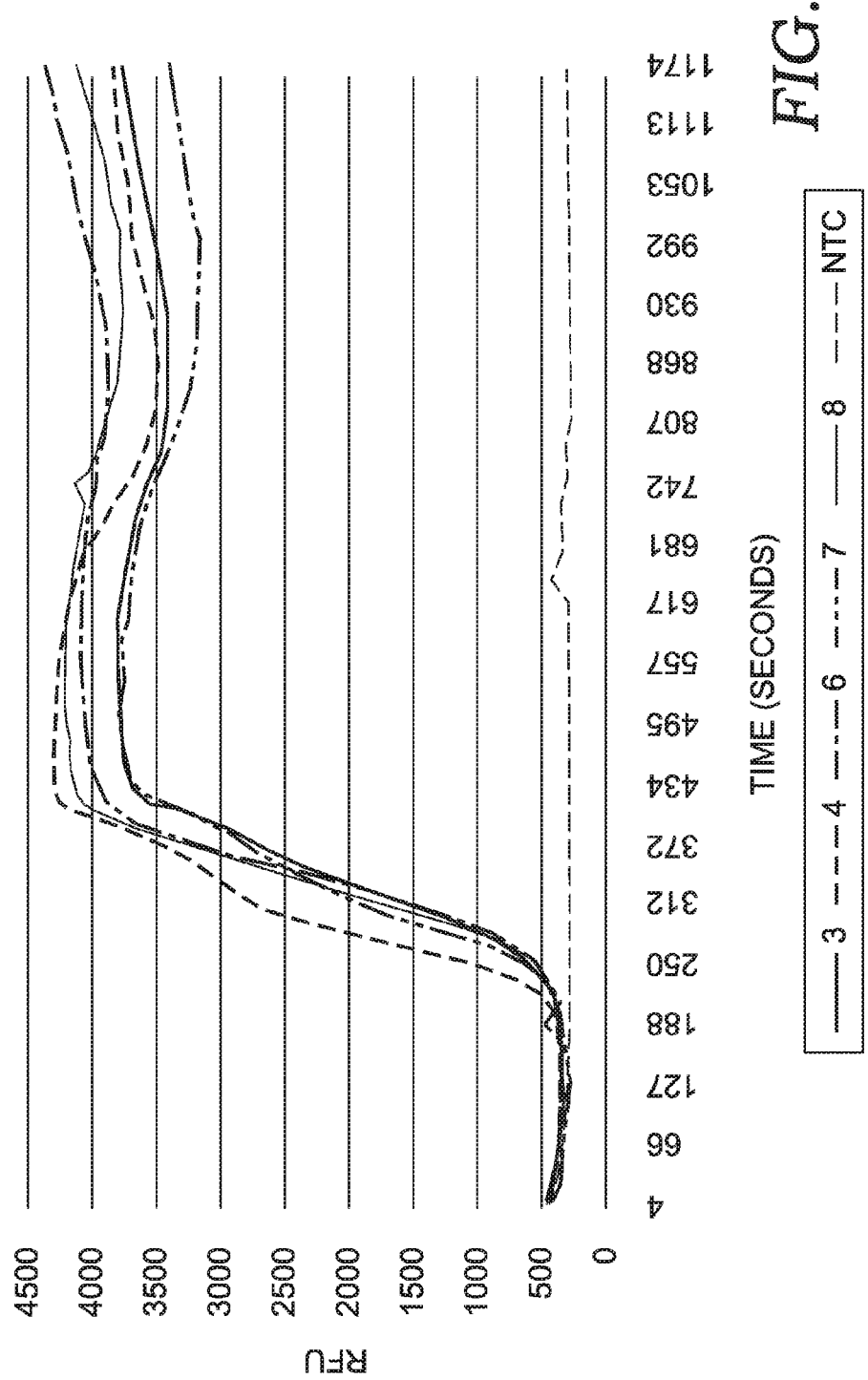

Recombinase Polymerase Amplification (RPA):

RPA reactions were carried out in 50 µl volumes using lyophilized materials prepared by TwistDx. Specific primers and probes targeting *C. difficile* toxin B gene, Shiga toxin stx1 gene, Shiga toxin stx2 gene, *Campylobacter* 16s rRNA gene, and *Salmonella* invA gene were used in the reactions. An Axxin T16 fluorescence reader was used for detecting amplification signals. The amplification signals of toxin B gene, Shiga toxin stx1 gene, Shiga toxin stx2 gene, *Campylobacter* 16s rRNA gene, and *Salmonella* invA gene from DNA purified by using a low percentage of organic solvent showed the same intensity as the DNA templates purified by using the boiling method or by using a commercial nucleic acid purification system, the Biomerieux NucliSENS easyMAG automated instrument. RPA tests for *Salmonella* invA gene (Sample 3, 4, 6, 7, and 8) and Shiga toxin stx2 gene (Sample 3 and 12) are shown in FIGS. 6A, 6B, 7A, and 7B. FIGS. 6A and 6B show *Salmonella* RPA tests with DNA extracted from stool samples. Crude DNA was extracted from five *Salmonella* positive samples (Sample 3, 4, 6, 7, and 8) using the boiling method (as illustrated in FIG. 6A) or an extraction buffer containing 3% of ethanol with incubation at 65° C. for 3 minutes (as illustrated in FIG. 6B). The amplification curves of *Salmonella* invA gene from the DNA samples are shown. NTC: no template control.

Figure 7A:
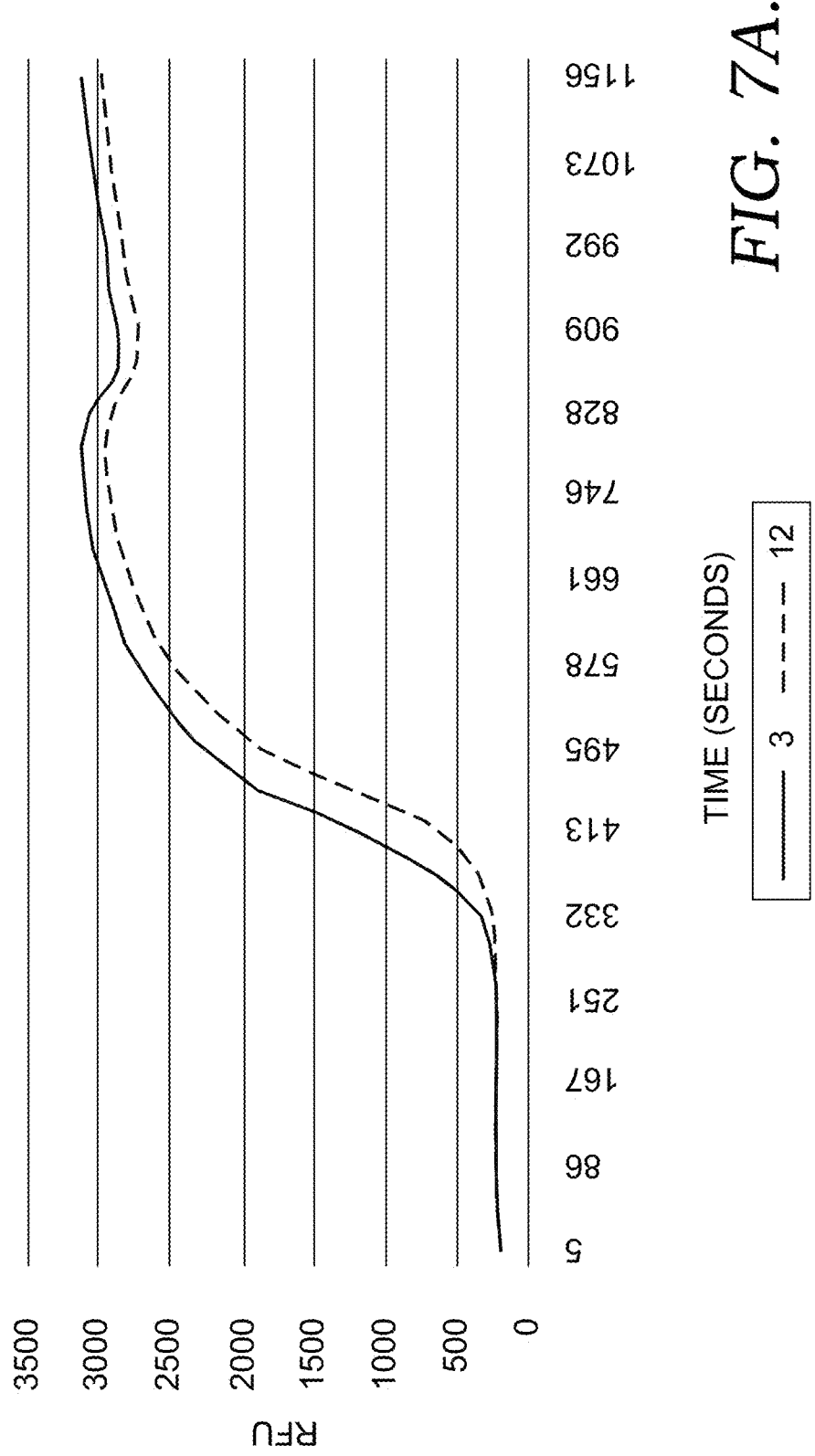
FIGS. 7A-7B depict graphs illustrating RPA tests to detect Shiga toxin stx2 gene in DNA extracted from stool samples.
Figure 7B:
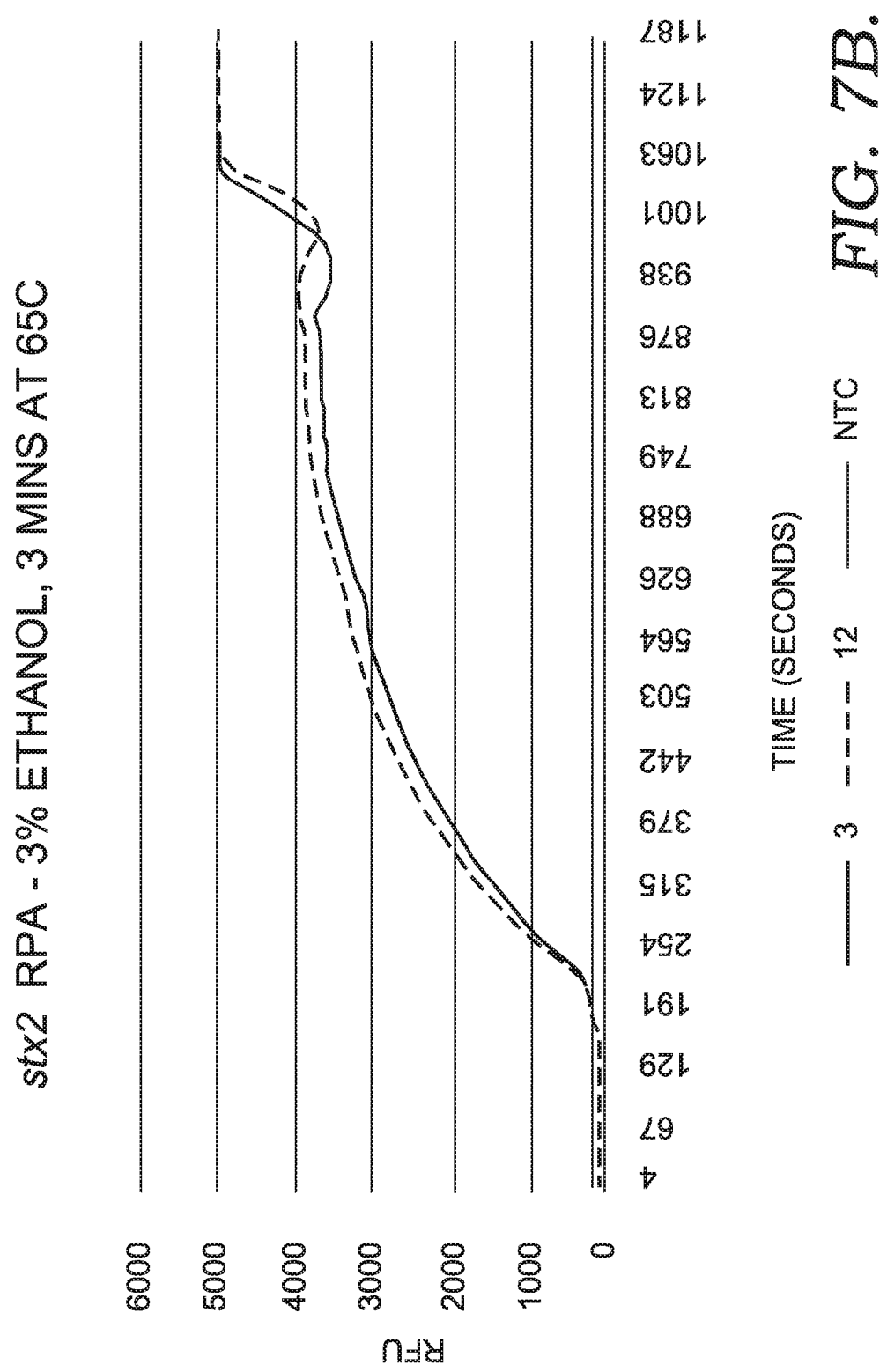

FIGS. 7A and 7B. illustrate RPA tests to detect Shiga toxin stx2 gene in DNA extracted from stool samples. Crude DNA was extracted from the two stx2 positive samples (Sample 3 and 12) using the boiling method (as illustrated in FIG. 7A) or an extraction buffer containing 3% of ethanol with incubation at 65° C. for 3 minutes (as illustrated in FIG. 7B). The amplification curves of Shiga stx2 gene from the DNA samples are shown.

For the DNA samples prepared from the boiling method or the method described in the present invention, the amplification starting time and the highest end point reading on the amplification curves were comparable. Using the composition and the method presented in the present invention, the results illustrate that the quality and quantity of DNA extracted from the human stool samples containing bacteria and parasites are sufficient for PCR and isothermal amplification.

Example 4

Comparison of Amplification of Nucleic Acids Extracted With or Without Ethanol Using Culture and Human Stool Samples Containing DNA and RNA Viruses This example is provided to evaluate efficiency of the buffer and the procedure for viral nucleic acid extraction. Adenovirus and norovirus positive clinical fecal samples were used in this example. Nucleic acid was extracted from those samples using the method described with reference to FIG. 1. A real-time PCR was carried out using the extracted nucleic acids and specific primers targeting a hexon gene (capsid protein II) of adenovirus to assess the quality and quantity of extracted nucleic acids from the adenovirus positive samples. The crude DNA extracted from the adenovirus positive samples showed very strong amplification of the adenovirus capsid protein II gene. When the same amount of DNA was used in the real-time PCR, the threshold cycle (Ct) values for DNA purified by using the method described with reference to FIG. 1 were almost the same as the DNA purified with the BioMerieux NucliSENS easyMAG automated instrument.

Figure 8:
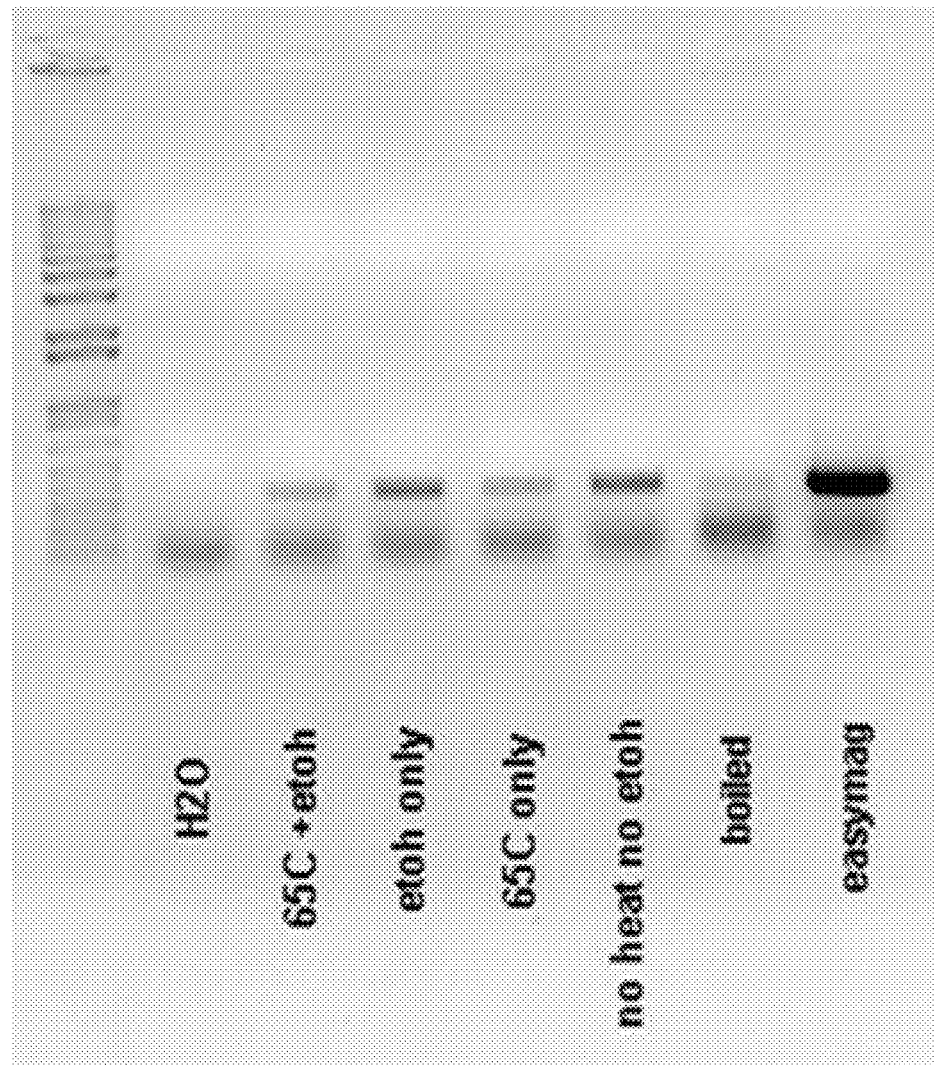
FIG. 8 depicts a Coomassie Blue-stained SDS-polyacrylamide gel of reverse transcription and PCR analysis of RNA extracted from a norovirus positive fecal sample.

FIG. 8 illustrates reverse transcription and PCR analysis of RNA extracted from a norovirus positive fecal sample. RNA extracted from a norovirus positive sample using the extraction buffer with 3% ethanol presented in the present invention was compared to the RNA extracted with boiling, no boiling, or incubation at 65° C. without organic solvent. RNA was also extracted using the BioMerieux NucliSENS easyMAG automated instrument and served as a control. Thermo Scientific Maxima H Minus First Strand cDNA Synthesis Kit with dsDNase was then used for reverse transcription. Following the reverse transcription, specific primers targeting the 3' end of ORF1 region of norovirus were used in a real time PCR. A 331 bp band of target region of norovirus from the organic solvent treated sample was amplified as illustrated in FIG. 8). The RNA purified with the BioMerieux NucliSENS easyMAG automated instrument at five folder higher amount of starting material was used as a control. The boiling step dramatically reduced the yield of RNA from the biological sample compared to the sample only treated with 3% of ethanol. PCR products were separated on a 1% agarose gel. The results demonstrate that the extraction buffer and the method presented in this claimed invention can robustly lyse virus to release nucleic acids well suited for PCR and reverse transcription PCR.

Example 5

Figure 9:
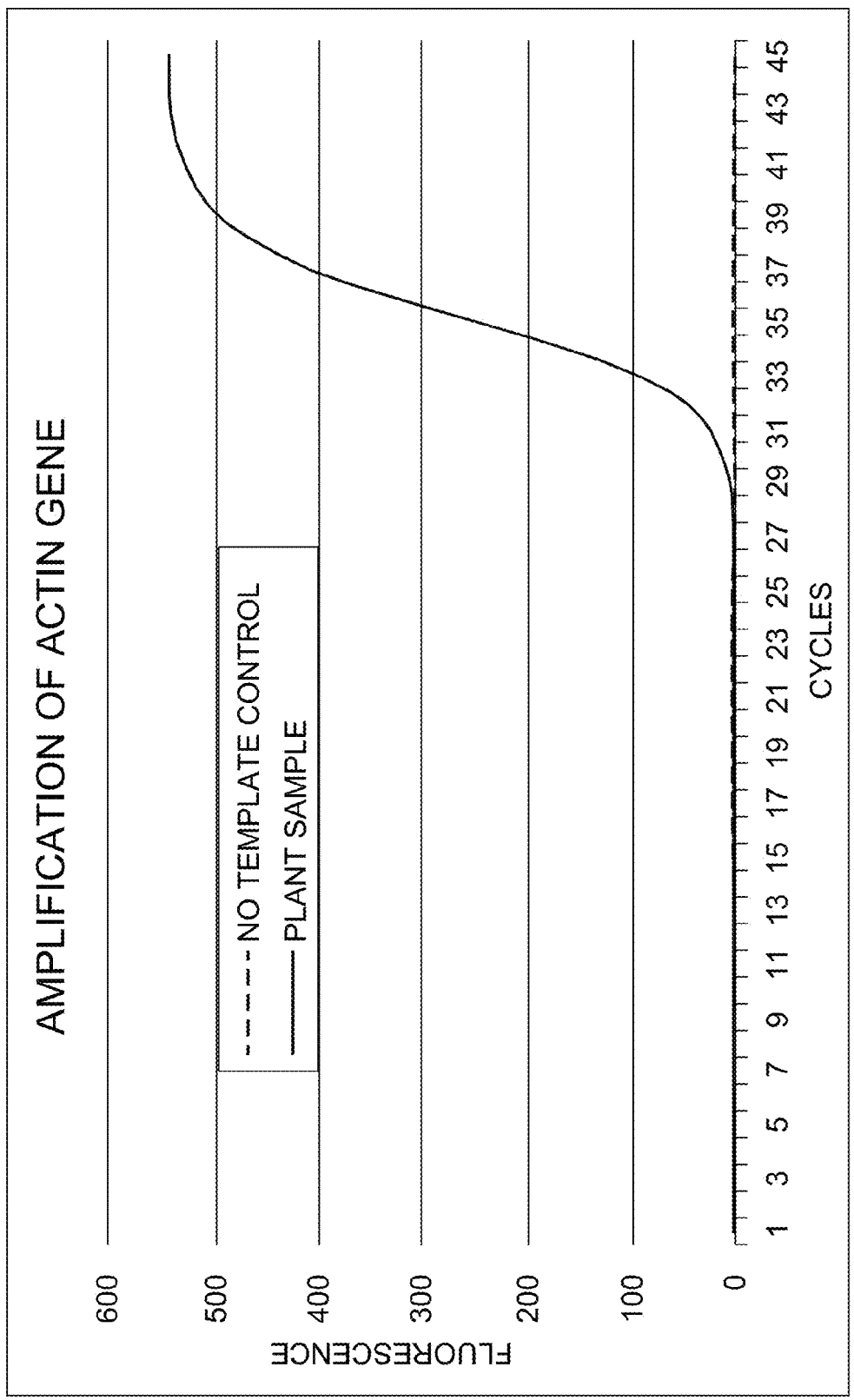
FIG. 9 depicts a graph illustrating PCR amplification with crude DNA extracted from the leaves of *Nicotiana benthamiana*.

Nucleic Acid Preparation Method in the Present Invention may be Applied to Plant Tissues This example is provided to test the capability of the extraction buffer presented in this claimed invention using plant tissues. FIG. 9 illustrates PCR amplification with crude DNA extracted from the leaves of *Nicotiana benthamiana*. Crude plant DNA was extracted using the method described in the present invention. Amplification of the actin gene is shown as a solid line. A dotted line represents no template control (NTC). Biomaterial was obtained from *Nicotiana benthamiana* plant leaves. Leaves were ground by using a mortar and transferred (100 µg) to a squeeze easy tube using the extraction buffer containing 3% ethanol. The tube was vortexed and one drop of buffer was squeezed through a charcoal filter tip into a 1.5 ml eppendorf tube containing 500 µl of PBS. The eppendorf tube was incubated at 65° C. for 3-5 minutes. A real-time PCR analysis was carried out using the extracted DNA and primers specifically targeting the actin gene of *Nicotiana benthamiana* on a SmartCycler. Successful PCR amplification of the plant actin gene demonstrated that the DNA templates extracted from plant tissues with the method described in the present invention can be used for PCR reactions (as illustrated in FIG. 9).

Example 6

DNA Extraction Method of the Present Claimed Invention may be Used to Eliminate or Reduce Amplification Inhibitors in Blood Samples The present example is provided to test inhibition of DNA amplification by blood. *C. difficile* positive clinical stool samples spiked with human blood at 5% concentration were used in this procedure. Isothermal reactions were carried out with DNA that was extracted from the spiked samples using the extraction buffer and method described with reference to FIG. 1. A swab of the bloody sample was added to a squeeze tube containing the extraction buffer with a 3% ethanol and the swab was snapped at the scored marker. One drop of extraction buffer was squeezed out to the reaction tube after an activated charcoal filter tip was placed on the top of the squeeze tube. After the reaction tube was incubated at 65° C. for 3 minutes, 50 µl of the extracted DNA was used for the *C. difficile* RPA reaction. The extracted nucleic acids were capable of amplifying tcdB gene and internal control in isothermal amplification reactions. However, when the extraction buffer without ethanol was used for the sample spiked with 5% human blood, amplification of the tcdB gene of *C. difficile* and internal control from the crude DNA was completely suppressed in the RPA test. The results show that the present claimed invention effectively removed inhibitors from the bloody sample.

Example 7

A Low Percentage of Organic Solvent may be Added Before, During, and After the Lysis Step During Nucleic Acid Extraction Process The human stool samples used in this procedure were from patients infected with *C. difficile*. Organic solvent was added at different steps during nucleic acid extraction. In the first experimental group, organic solvent was directly added to the stool samples. Stool samples (100 µl) were added to an eppendorf tube containing 250 µl of PBS with a 3% of ethanol and vortexed for 10 seconds. They were then transferred to a squeeze easy tube containing the extraction buffer without ethanol. After that, DNA was extracted following the method described with reference to FIG. 1. In the second experimental group, ethanol was added after the stool samples were lysed. Stool samples (100 µl) were added to a squeeze easy tube containing the extraction buffer without ethanol and a filter tip was snapped on the top of the tube. The squeeze easy tube was vortexed and about 100 µl of the lysed sample was squeezed out from the tube. Three percent of ethanol was added to the 100 µl of lysed sample and vortexed. One drop of the lysed samples (about 25-30 µL) was diluted in a reaction tube and incubated at 65° C. for 3 minutes. The crude DNA was then used directly for PCR amplification. In the third experimental group, organic solvent was added to the extraction buffer. Crude DNA was extracted from stool samples with the extraction buffer containing 3% ethanol following the method describe with reference to FIG. 1.

RPA reactions were carried out in 50 µl volumes using the crude DNAs prepared with the methods mentioned above and lyophilized materials prepared by TwistDx. Specific primers and probes targeting *C. difficile* toxin B gene were used in the reaction. An Axxin T16 fluorescence reader was used for detecting signals from DNA amplification. Addition of ethanol at different steps during nucleic acid extraction made no difference in the signal intensity of amplification from the extracted DNA; successful amplification was achieved with all crude DNA that were extracted with different procedures (as illustrated in FIG. 10).

Figure 10:
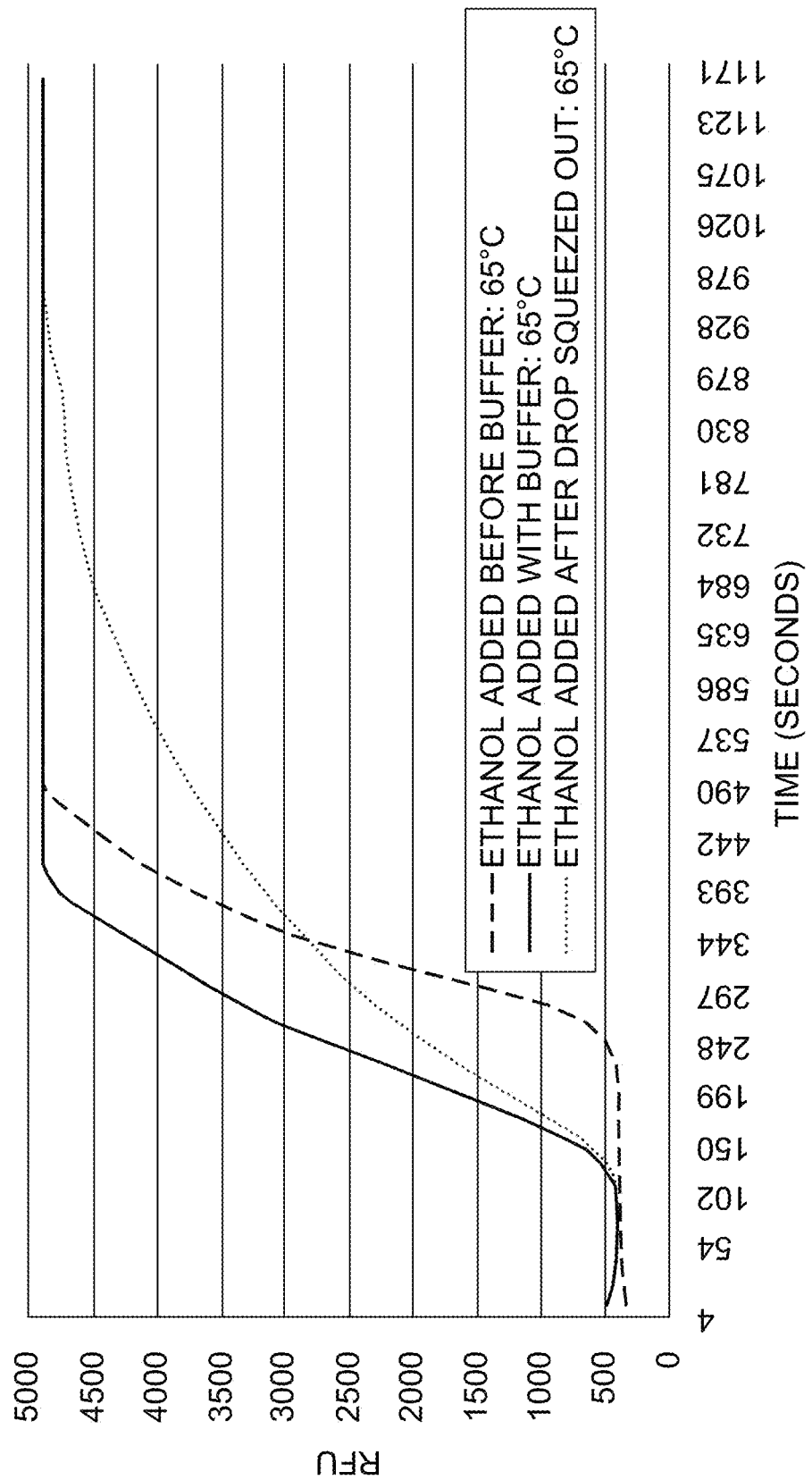
FIG. 10 depicts a graph illustrating inhibitors of amplification can be eliminated by addition of organic solvent at different steps during nucleic acid extraction.

FIG. 10 illustrates that inhibitors of amplification can be eliminated by addition of organic solvent at different steps during nucleic acid extraction. Crude DNA was extracted from human stool samples. Ethanol (3%) was added to the extraction buffer (solid line), to the diluted stool samples (dash line), or to the lysates of stool samples (dotted line), followed by incubation at 65° C. for 3 minutes. Amplification of *C. difficile* toxin B gene in the extracted DNA was measured with a *C. difficile* RPA assay. The results indicate that the quality and quantity of DNA extracted using the present method from the human stool samples are appropriate for PCR and isothermal amplification, and that organic solvent treatment can be applied prior to nucleic acid extraction, during extraction, or after extraction before diluted in a PCR or an isothermal reaction buffer.

Example 8

Alternatives to Ethanol in Nucleic Acid Extraction Buffer

A group of organic solvents were tested as alternatives to ethanol in the nucleic acid extraction buffer presented in this present invention; examples include acetone, methanol, isopropanol, butanol, and DMSO. Crude DNA was extracted from two positive (Sample 6654 and 6799) and two negative *C. difficile* samples (Sample 4268 and 6901) by using the method described with reference to FIG. 1. The crude DNA prepared from these four samples without the addition of organic solvent presented strong inhibitory effects on amplification, resulting in failed amplification of internal control (Table 1, column 2). Each organic solvent was used to replace ethanol in the extraction buffer. The *C. difficile* RPA test was employed to evaluate the quality and quantity of DNA extracted with different organic solvents. The *C. difficile* RPA test was scored as (1) failure-no detectable amplification signal, (2) compromised less amplicon signal compared to controls, or (3) nominal-amplicon similar to controls. All organic solvents gave strong signals with known positive samples. (Table 1). These results demonstrate that organic solvents, including ethanol, acetone, butanol, DMSO, but not limit to these organic solvents, can be used in the present invention.

TABLE 1

Testing alternatives to ethanol in the *C. difficile* RPA assay

| sample | no solvent | ethanol | acetone | DMSO | butanol |
|---|---|---|---|---|---|
| 4268 (−) | invalid | − | − | − | − |
| 6654 (+) | invalid | +++ | ++ | + | + |
| 6799 (+) | invalid | +++ | +++ | ++ | +++ |
| 6901 (−) | invalid | − | − | − | − |

TABLE 2

DNA amplification with concentrations of ethanol ranging from 0.5% to 15%.

| | | | % ethanol in extraction buffer with Heating to 65° C. for 3 minutes | | | | | |
|---|---|---|---|---|---|---|---|---|
| | | | 0.50% | 3% | 5% | 8% | 10% | 15% |
| real time PCR (Ct) | gluD of C. difficile | Sample 4 | 30.04 | 30.12 | 29.98 | 30.39 | 30.69 | n/a |
| | | Sample 16 | 34.97 | 33.59 | 36.35 | 36.21 | 36.75 | n/a |
| | tcdB of C. difficile | Sample 4 | 32.07 | 33.45 | 32.11 | 32.55 | 32.48 | n/a |
| | | Sample 16 | 35.08 | 40.08 | 37.91 | 39.12 | 40.95 | n/a |
| RPA | tcdB of C. difficile | Sample 16 | ++ | ++ | ++ | ++ | ++ | ++ |

In addition, different concentrations of organic solvent (from 0.5% to 20%) have been tested in the extraction buffer. Amplification of the gluD and tcdB genes of *C. difficile* from crude DNA extracts (Sample 4 and 16) did not show significant difference. The Ct values of real-time PCR were similar for crude DNA extracted with different concentrations of ethanol (Table 2). The RPA results show that the concentration of ethanol ranging from 0.5% to 15% in extraction buffer did not interfere with DNA amplification (Table 2).

Example 9

Comparison of Quality and Quantity of Nucleic Acid Extracted in Present Claimed Invention Versus an Automated System in Multiplex PCR and Multiplex Isothermal Amplification DNA was extracted from clinical fecal samples that were positive for Shiga toxin gene stx1 and stx2 by using the DNA extraction buffer presented in the present invention and following the procedure described with respect to FIG. 1. In addition, DNA purified from Biomerieux NucliSENS easyMAG served as a control. Specific primers targeting stx1 and stx2 genes were utilized in the multiplex PCR and multiplex RPA reactions. Using the DNA extracted from those samples, amplification signals of both stx1 and stx2 genes were detected in the multiplex PCR by a PCR instrument and in multiplex RPA reactions by an Axxin T16 fluorescence reader. DNA extracted using a 3% of ethanol presented in the present invention gave the same signals of amplification of stx1 and stx2 as the DNA purified from Bionerieux NucliSENS easyMAG. This indicated that the quality and quantity of crude nucleic acids extracted by using the method of the present invention is equivalent to the DNA purified from Biomerieux NucliSENS easyMAG automated instrument.

The present invention has been described in relation to particular embodiments, which are intended in all respects to be illustrative rather than restrictive. Since many possible embodiments may be made of the claimed invention without departing from the scope thereof, it is to be understood that all matter herein set forth is to be interpreted as illustrative and not in a limiting sense. Alternative embodiments will become apparent to those of ordinary skill in the art to which the present claimed invention pertains without departing from its scope.

From the foregoing, it will be seen that this invention is one well adapted to attain all the ends and objects set forth above. It will be understood that certain features and subcombinations are of utility and may be employed without reference to other features and subcombinations. This is contemplated and within the scope of the claims.

What is claimed:

1. A method for treating a biological sample for nucleic acid extraction, the method comprising:
   obtaining a biological sample, the biological sample comprising one or more of stool, blood, saliva, or urine;
   diluting the biological sample in an extraction buffer comprising 0.5 to 20 wt. % organic solvent to form a mixture;
   incubating the mixture at a temperature from 15° C. to 35° C. for five seconds to thirty minutes, to cause nucleic acid present in the biological sample to be extracted from at least a portion of the biological sample for further processing;
   separating at least a portion of the extraction buffer and at least a portion of the nucleic acid from the biological sample;
   forming an amplification mixture comprising: the at least a portion of the extraction buffer; the at least a portion of the nucleic acid; and one or more amplification reaction buffers; and
   incubating the amplification mixture for 1 to 10 minutes at 25° C. to 70° C.

2. The method of claim 1, wherein said biological sample comprises one or more human specimens, bacteria, viruses, parasites, stool samples, body fluids, plants, or cultures.

3. The method of claim 1, wherein said organic solvent comprises one or more of acetone, methanol, ethanol, isopropanol, butanol, or dimethyl sulfoxide (DMSO).

4. The method of claim 1, wherein the extraction buffer comprises 3 wt. % to 10 wt. % organic solvent, wherein the organic solvent comprises ethanol, acetone, or a combination thereof.

5. The method of claim 1, wherein separating at least a portion of the nucleic acid from the biological sample comprises filtering the mixture with a filter.

6. The method of claim 5, wherein the filter has a pore size of from 50 gm to 250 gm.

7. The method of claim 5, wherein the filter comprises one or more of a porous plastic, porous polymeric fiber, or porous glass fiber.

8. The method of claim 7, wherein the filter comprises a glass fiber filter embedded with activated charcoal.

9. The method of claim 1, wherein said biological sample is incubated for 3-5 minutes at 25° C. to 70° C.

10. The method of claim 1, wherein said incubation temperature is between 50° C. and 65° C.

11. The method of claim 1, wherein the organic solvent may eliminate the need of one or more of heating, enzymatic digestions, incubations, separation, nucleic acid precipitation, or elution.

12. The method of claim 11, wherein said heating is at a temperature of 95° C. or above.

13. The method of claim 1, wherein amplification reaction buffers are buffers suitable for isothermal amplification, PCR, sequencing, genotyping, and hybridization.

14. The method of claim 13, wherein isothermal comprises nicking enzyme associated reaction (NEAR), recombinase polymerase amplification (RPA), loop mediated isothermal amplification (LAMP), strand displacement amplification, helicase-dependent amplification, rolling circle amplification, and other isothermal amplification methods.

15. The method of claim 1, further comprising amplifying the at least a portion of the nucleic acid in an amplification reaction.

16. The method of claim 15, wherein the amplifying is done using the extraction buffer with organic solvent but no heating.

17. The method of claim 15, wherein the amplifying is done using the extraction buffer with organic solvent with heating.

18. The method of claim 1, wherein the extraction buffer comprises an extraction buffer used for nucleic acid amplification.

19. A method for treating a biological sample for nucleic acid extraction, the method comprising:
   obtaining a biological sample, the biological sample comprising a stool sample;
   diluting the biological sample in an extraction buffer comprising 0.5 to 20 wt. % organic solvent to form a mixture;
   incubating the mixture at a temperature from 15° C. to 70° C. for five seconds to thirty minutes, to cause nucleic acid present in the biological sample to be extracted from at least a portion of the biological sample for further processing;
   separating at least a portion of the extraction buffer and at least a portion of the nucleic acid from the biological sample; and
   forming an amplification mixture comprising: the at least a portion of the extraction buffer; the at least a portion of the nucleic acid; and one or more amplification reaction buffers.

20. A method for treating a biological sample for nucleic acid extraction, the method comprising:
   obtaining a biological sample, the biological sample comprising one or more of stool, blood, saliva, or urine;
   diluting the biological sample in an extraction buffer comprising 0.5 to 20 wt. % organic solvent to form a mixture;
   incubating the mixture at a temperature from 15° C. to 35° C. for five seconds to thirty minutes, to cause nucleic acid present in the biological sample to be extracted from at least a portion of the biological sample for further processing;
   separating at least a portion of the extraction buffer and at least a portion of the nucleic acid from the biological sample to provide a separated nucleic acid;
   adding an organic solvent to at least a portion of the separated nucleic acid to a concentration of from 0.5 to 20 wt. % to form a treated nucleic acid;
   forming an amplification mixture comprising the at least a portion of the separated nucleic acid; and one or more amplification reaction buffers; and
   amplifying the at least a portion of the nucleic acid present in the amplification mixture in an amplification reaction.

\* \* \* \* \*